United States Patent [19]

Gross

[11] Patent Number: 5,179,202
[45] Date of Patent: Jan. 12, 1993

[54] REACTION PRODUCT OF GRAFTED DEXTRANOMER AND A PHTHALOCYANINE DYE

[75] Inventor: Gian-Andrea Gross, Marsens, Switzerland

[73] Assignee: Nestec S.A., Vevey, Switzerland

[21] Appl. No.: 615,007

[22] Filed: Nov. 16, 1990

[30] Foreign Application Priority Data

Dec. 27, 1989 [EP]  European Pat. Off. ........... 89123930

[51] Int. Cl.$^5$ .................... C07H 15/04; C07H 23/00; C08B 37/00
[52] U.S. Cl. .................................. 536/120; 536/121; 536/112; 536/113; 536/1.1
[58] Field of Search ............... 536/120, 121, 112, 113, 536/56, 84, 101, 102, 106

[56] References Cited

U.S. PATENT DOCUMENTS

| | | | |
|---|---|---|---|
| 4,178,438 | 12/1979 | Haase et al. | 536/30 |
| 4,359,419 | 11/1982 | Pociluyko | 536/56 |
| 4,432,900 | 2/1984 | Pociluyko | 536/56 |
| 4,490,525 | 12/1984 | Hayatsu et al. | 536/121 |
| 4,546,161 | 10/1985 | Harvey et al. | 536/51 |

FOREIGN PATENT DOCUMENTS

| | | |
|---|---|---|
| 0090610 | 5/1983 | European Pat. Off. . |
| 0157549 | 9/1985 | European Pat. Off. . |

OTHER PUBLICATIONS

Gross et al., "An Efficient and Convenient Method for the Purification of Mutagenic Heterocyclic Amines in Heated Meat Products" *Carcinogenesis*, vol. 10, No. 7, pp. 1175-1182: 1989.

*Primary Examiner*—Johnnie R. Brown
*Assistant Examiner*—Everett White
*Attorney, Agent, or Firm*—Vogt & O'Donnell

[57] ABSTRACT

Polycyclic mutagens are removed from aqueous or organic solutions by contacting the solution with a grafted dextranomer adsorbent which contains hydroxypropyl groups covalently linked to a reactive phthalocyanine dye.

7 Claims, 1 Drawing Sheet

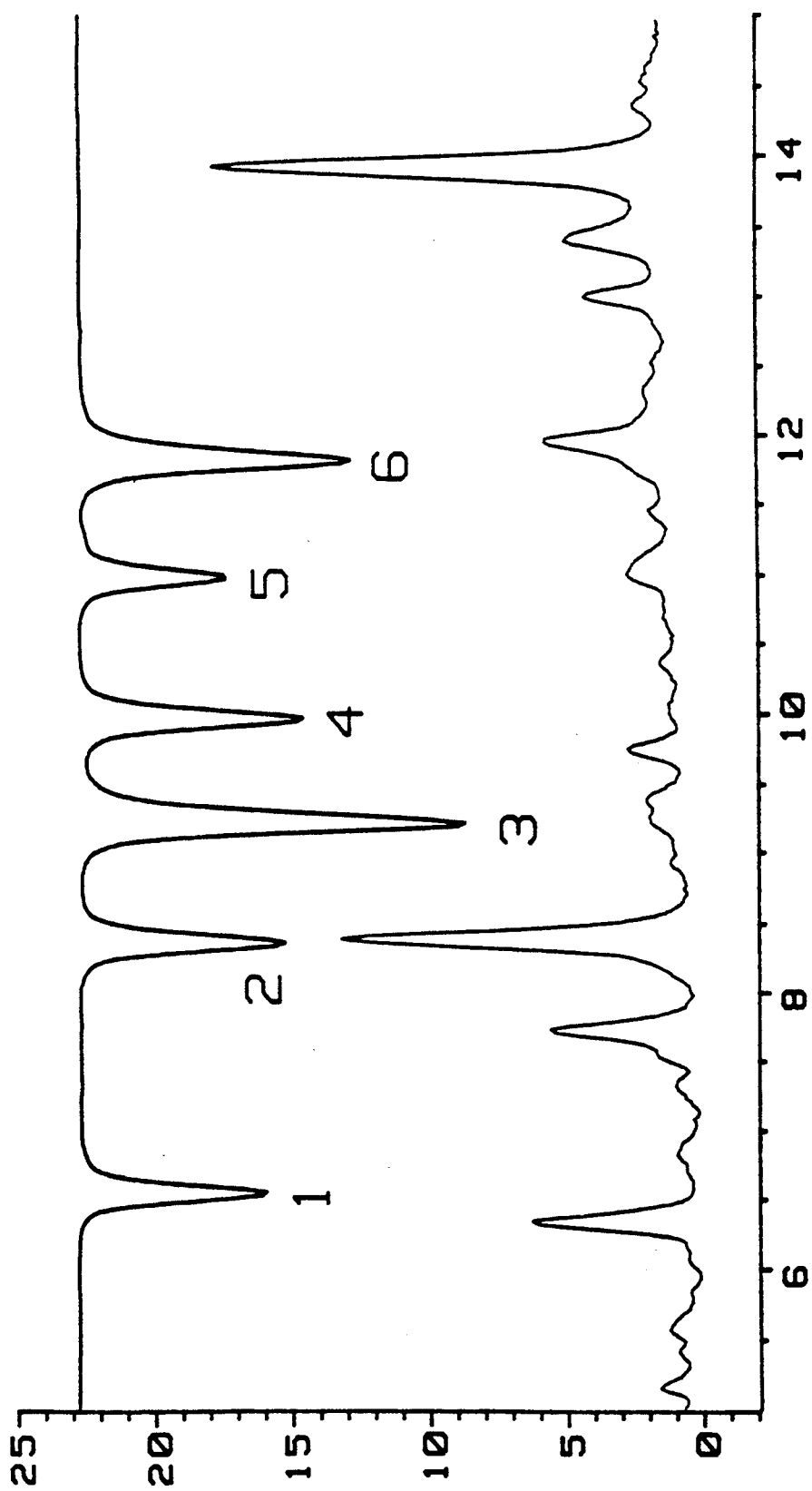

REACTION PRODUCT OF GRAFTED DEXTRANOMER AND A PHTHALOCYANINE DYE

BACKGROUND OF THE INVENTION

This invention relates to a reaction product of a grafted dextranomer and a phthalocyanine dye. The invention also relates to the use of this reaction product for selectively adsorbing mutagenic heterocyclic amines.

For some time, the mutagenic substances present in our environment and in certain of our foods have become a major subject of concern on account of their effect on the health of human beings as potential carcinogenic agents. Accordingly, there is a considerable need for techniques enabling such substances to be analyzed and eliminated.

It is known that compounds of the phthalocyanine type have the property of forming stable complexes with polycyclic mutagenic substances. This property has been utilized for preparing products for the selective adsorption of polycyclic mutagenic substances present in essentially aqueous media by reaction of phthalocyanines containing a reactive group with organic or inorganic solid materials. For example, European Patent 90 610 describes a method for adsorbing polycyclic mutagenic substances using an adsorption product prepared from cellulose and a phthalocyanine dye containing a reactive group. According to U.S. Pat. No. 4,490,525, products for the adsorption of polycyclic mutagenic substances are prepared from polysaccharides of the agarose or dextrin type chemically activated beforehand, onto which reactive phthalocyanines are grafted. According to European Patent 157 549, phthalocyanines containing a reactive group are chemically fixed to silica gel onto which aminopropyl residues are grafted. However, with all these adsorbents for the polycyclic mutagenic substances mentioned by way of example, affinity for those mutagenic substances is conferred almost entirely by the phthalocyanine residue and does not utilize any intrinsic properties of affinity for the mutagenic substances mentioned which the solid starting material used for the production of the adsorbent product might have. In addition, these materials not only have affinity for the polycyclic mutagenic substances mentioned, but also for a certain number of other substances which might also be present in the media containing the mutagenic substances mentioned, so that the selectivity of these adsorbent materials with respect to the mutagenic substances mentioned is often mediocre. On the other hand, the adsorbent materials mentioned by way of example only work when the mutagenic substances are present in essentially aqueous media. Accordingly, they cannot be used in every case where contact with the mutagenic substances would have to take place in an organic solvent.

It is known from the literature that other adsorbent materials than those containing phthalocyanine residues have a certain affinity for polycyclic mutagenic substances. For example, in Carcinogenesis 1989, 10(7), 1175-1182, G. A. Gross et al. showed that a material produced from dextranomer, which is a polymer of the dextran type crosslinked by 2-hydroxy-1,3-propylene bridges and onto which hydroxypropyl groups are grafted (hereinafter referred to as grafted dextranomer), shows a higher adsorption selectivity with respect to polycyclic mutagenic substances than the majority of other known adsorbents which do not contain phthalocyanine residues For example, the utilization of this grafted dextranomer for analytical purposes enables the precision of methods for detecting polycyclic mutagenic substances in food products to be simplified and increased. However, in some cases, for example when these mutagenic substances are present in media of high chemical complexity or when their concentration in these media is particularly low, the selectivity of this grafted dextranomer with respect to the mutagenic substances mentioned may no longer be sufficient to enable the substances in question to be detected by analytical methods.

SUMMARY OF THE INVENTION

The present invention relates to a reaction product of a grafted dextranomer containing hydroxypropyl groups and a phthalocyanine dye optionally comprising a metal atom and bearing a reactive group capable of reacting with the hydroxy group of the grafted dextranomer to form a covalent bond therewith. The metal atom is selected from copper, iron, nickel, cobalt and aluminium atoms and is preferably the copper atom.

The reaction product according to the invention is capable of selectively adsorbing polycyclic mutagenic and carcinogenic substances in solution in an aqueous or organic medium. According to the invention, it has been found that, when a phthalocyanine containing a reactive group is chemically attached to grafted dextranomer, a reaction product is obtained which combines a remarkable capacity for adsorbing polycyclic mutagenic substances with a remarkable selectivity with respect to those substances and an equally remarkable capacity for restoring those substances by desorption.

DETAILED DESCRIPTION OF THE INVENTION

The reaction product according to the invention is prepared by reaction of the hydroxyl functions of the grafted dextranomer with the reactive group of the phthalocyanine using any of the methods for fixing dyes to fibrous materials commonly used in the dye industry. Examples of such reactive groups of phthalocyanines which may be used for this reaction are the dihalotriazinyl, monohalotriazinyl, trihalopyrimidinyl, sulfatoethyl sulfonyl, chloroethyl sulfonyl, dihaloquinoxalinyl, dihalopyridazonyl, sulfatoethyl sulfonamidyl, mono- or dihalopyrimidinyl, dihalophthalazinyl, acrylamidyl, vinyl sulfonyl, halobenzothiazolyl, methylolamino and β-sulfatoethyl sulfonyl phenyl aminosulfonyl groups.

The reactive phthalocyanine dyes well known in the dye industry are advantageously used as the phthalocyanines containing a reactive group.

Although grafted dextranomer may readily be prepared from dextranomer by grafting hydroxypropyl residues onto the hydroxyl functions, the grafted dextranomer used in accordance with the invention is preferably selected from any of the commercially available finished materials, such as for example those manufactured by Pharmacia Fine Chemicals AB, Uppsala (Sweden) under the name of SEPHASORB or SEPHADEX, of which the unit structure is shown below:

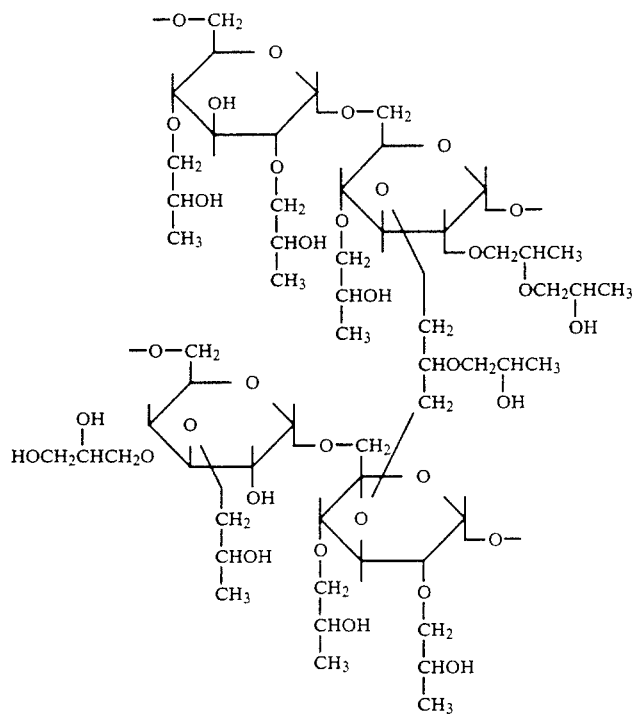

In one preferred embodiment of the product according to the invention, the grafted dextranomer used is the Pharmacia product marketed under the name of SEPHASORB HP Ultrafine while the reactive phthalocyanine dye is Reactive Blue 21 of the Color Index (C. I. Reactive Blue 21), for example marketed by Hoechst AG, Frankfurt (Federal Republic of Germany) under the name of REMAZOL Bleu Turquoise (Turquoise Blue) G133.

The mutagenic substances with which the present invention is concerned are aromatic or heterocyclic compounds containing at least two fused rings. The following compounds are examples of such mutagenic substances: Trp-P-1 (3-amino-1,4-dimethyl-5H-pyrido[4,3-b]indole),Trp-P-2 (3-amino-1-methyl-5H-pyrido[4,3-b]indole), Glu-P-1 (2-amino-6-methyldipyrido[1,2-a:3',2'-d]imidazole,Glu-P-2 (2-aminodipyrido[1,2-a:3',2'-d]imidazole, amino-α-carboline (2-amino-9H-pyrido[2,3-b]indole), aminomethyl-α-carboline (2-amino-3-methyl-9H-pyrido[2,3-b]indole), IQ (2-amino-3-methylimidazo[4,5-f]quinoline, 2-acetylaminofluorene, ethidium bromide, MeIQ$_x$ (2-amino-3,8-dimethylimidazo[4,5-f]quinoxaline), 9-aminoacridine, quinacrine, 8-methoxypsoralene, chloropromazine, harmane, norharmane (β-carboline), MeIQ (2-amino-3,4-dimethylimidazo[4,5-f]quinoline), 4,8-DiMeIQx (2-amino-3,4,8-trimethylimidazo[4,5-f]quinoxaline, 7,8-DiMeIQx (2-amino-3,7,8-trimethylimidazo[4,5-f]quinoxaline, 4,7,8-TriMeIQx (2-amino-3,4,7,8-tetramethylimidazo[4,5-f]quinoxaline and benzo[a]pyrene.

The present invention also relates to the use of the reaction products, comprising selectively adsorbing onto said reaction product polycyclic organic substances, more particularly heterocyclic amines, in solution in aqueous or organic media. The invention enables the polycyclic mutagenic substances typically present in very small quantities (ppb) in products intended for consumption or in biological media to be eliminated or analyzed.

If it is desired to eliminate the mutagenic substances, selective adsorption onto the reaction product is carried out and the adsorption column is either discarded or is regenerated by eluting the mutagenic substances. If it is desired to analyze the mutagenic substances, selective adsorption is carried out and the mutagenic substances are desorbed and recovered in a concentrated form.

In addition, the adsorption capacity and selectivity are in evidence not only when the mutagenic substances are present in an aqueous medium, but also when they are present in an organic solvent. In the present context, an organic solvent is understood to be not only a polar or protic solvent, such as for example methanol, ethanol or acetone, but also a weakly polar or apolar solvent, such as ethyl acetate, diethyl ether, halogenated solvents or volatile hydrocarbons. Dichloromethane is preferably used as the organic solvent.

The adsorption product according to the invention is contacted with the polycyclic mutagenic substances by addition of the grafted dextranomer to an aqueous or organic solution containing the mutagenic substances and by stirring this mixture at ambient temperature. In one preferred embodiment, contacting is carried out by filling a column with the adsorption product and then passing an aqueous or organic solution containing the mutagenic substances through the column.

If desired, the desorption of the mutagenic substances from the reaction product according to the invention can be carried out by contacting the reaction product, onto which the mutagenic substances are adsorbed, with a neutral or slightly acidic or alkaline solvent, such as for example methanol or a mixture of methanol with acetic acid or trifluoroacetic acid or a mixture of methanol with ammonia. In this case, contacting may be carried out either by immersion of the adsorption product in the desorption solvent or preferably by passing the desorption solvent through a column containing the adsorption product.

The capacity of the reaction product according to the invention for selectively adsorbing and restoring the polycyclic mutagenic substances may be utilized in the practical application of methods for eliminating or analyzing these mutagenic substances, for example those which can be found in certain foods, into tobacco smoke, in waters intended for consumption or in biological media.

EXAMPLES

The following Examples are intended to illustrate the invention in more detail without limiting it in any way.

EXAMPLE 1

Preparation of the reaction product according to the invention 100 g SEPHASORB HP are heated for 2 hours at 80° C. in a solution of 5 g REMAZOL turquoise blue, 12 g sodium carbonate and 30 g sodium sulfate dissolved in 600 ml water. The mixture is left to cool and the filtered product is washed with 1 liter water and then with 1 liter of a 1:1 mixture of methanol and concentrated ammonia. The end product is then continuously washed with 7 l methanol and, finally, is thoroughly centrifuged and dried in vacuo. The product according to the invention, hereinafter referred to as SEPHASORB blue, is thus obtained.

The product is characterized by its content of copper ions by atomic adsorption spectrophotometry. The copper content is 520 μg/g SEPHASORB blue.

EXAMPLE 2

Adsorption capacity of SEPHASORB blue for polycyclic mutagenic substances

A 2 ml extraction column is charged with the reaction product of Example 1 suspended in a methanolic solution to a volume of 0.5 ml SEPHASORB blue. The lower end of the column is connected by a polytetrafluoroethylene tube to a UV recorder adjusted for a reading at 254 nm. The column is rinsed with a little methanol, after which dichloromethane (DCM) is passed through until the recorder shows a stable base line. A $10^{-5}$ molar solution of a mutagenic substance in DCM is then passed through the column at a rate of 0.3 ml/min. up to saturation of the SEPHASORB blue by the mutagenic substance which is measured on the recorder at the inflection point of the adsorption curve (cf. Liska et al., J. High Res. Chrom., 1989, 12, 577-590).

The reaction product according to the invention has an adsorption capacity for IQ of 200 μg per ml SEPHASORB blue.

If the operation is repeated with a column of untreated SEPHASORB HP, a value below 10 μg per ml SEPHASORB HP is obtained.

EXAMPLE 3

Application of the product according to the invention in a method for analysis of the polycyclic substances present in meat extracts A basic meat extract fraction prepared from 1 g meat extract (by the method described by G. A. Gross et al. in the Article mentioned on page 2) contained in 10 ml DCM is passed through a 4 ml column containing 1 ml SEPHASORB blue at a rate of 0.4 ml/min. The column is rinsed with 5 ml DCM. It is then desorbed by elution with 10 ml of a DCM solution containing 15% methanol and 0.1% concentrated ammonia. The eluate is evaporated to dryness.

Two procedures may then be adopted. Either the solid residue is dissolved in 100 μl methanol, the resulting solution is filtered through a microfilter and an aliquot of the solution is injected into an HPLC chromatograph with UV detection.

Or, if it is desired to obtained greater sensitivity of measurement (below 0.1 ppm), the residue is dissolved in 100 μl methanol and made up with 2 ml water. The solution obtained is washed in a column of SEPHASORB HP and evaporated to dryness. The residue is then taken up in 100 μl methanol and the resulting solution is filtered through a microfilter and injected into an HPLC chromatograph.

The accompanying FIGURE shows a chromatogram obtained by the second method. The upper curve is the chromatogram of a reference substance while the lower curve is the chromatogram of the analyzed meat extract. The abscissa gives the time in minutes while the ordinate gives the content of mutagenic compound.

Compound 1 is IQx while compound 2 is MeIQx, 3=IQ, 4=7,8-DiMeIQx, 5=4,8-DiMeIQx and 6=MeIQ.

I claim:

1. A grafted dextranomer containing hydroxypropyl groups covalently linked to a reactive phthalocyanine dye.

2. A grafted dextranomer according to claim 1 wherein the phthalocyanine dye contains a metal atom.

3. A grafted dextranomer according to claim 2 wherein the metal atom is a member selected from the group consisting of copper, iron, nickel, cobalt and aluminum.

4. A grafted dextranomer according to claim 1 wherein the grafted dextranomer is SEPHASORB HP.

5. A grafted dextranomer according to claim 1 wherein the phthalocyanine dye is REMAZOL turquoise.

6. A grafted dextranomer according to claim 1 wherein the grafted dextranomer is SEPHASORB HP and wherein the phthalocyanine dye is REMAZOL turquoise.

7. A grafted dextranomer according to claim 1 wherein the reactive phthalocyanine dye is covalently linked to the grafted dextranomer through a reactive group selected from the group of reactive groups consisting of dihalotriazinyl, monohalotriazinyl, trihalopyrimidinyl, sulfatoethyl sulfonyl, chloroethyl sulfonyl, dihaloquinoxalinyl, dihalopyridaxonyl, sulfatoethyl sulfonamidyl, mono- or dihalopyrimidinyl, dihalophthalazinyl, acrylamidyl, vinyl sulfonyl, halobenzothiazolyl, methylolamino and β-sulfatoethyl sulfonyl phenyl aminosulfonyl.

* * * * *